US010545090B2

(12) United States Patent
Karlsson (10) Patent No.: US 10,545,090 B2
(45) Date of Patent: Jan. 28, 2020

(54) METHOD AND SYSTEM FOR MORE RELIABLE DETERMINATION OF INTERACTION PARAMETERS FOR LOW AFFINITY ANALYTES

(75) Inventor: Olof Karlsson, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days.

(21) Appl. No.: 13/512,362

(22) PCT Filed: Nov. 29, 2010

(86) PCT No.: PCT/SE2010/051310
§ 371 (c)(1),
(2), (4) Date: May 29, 2012

(87) PCT Pub. No.: WO2011/065912
PCT Pub. Date: Jun. 3, 2011

(65) Prior Publication Data
US 2012/0244637 A1 Sep. 27, 2012

(30) Foreign Application Priority Data

Nov. 30, 2009 (SE) ...................................... 0950913
Dec. 30, 2009 (SE) ...................................... 0951035

(51) Int. Cl.
*G01N 33/557* (2006.01)
*G01N 21/552* (2014.01)

(52) U.S. Cl.
CPC ......... *G01N 21/553* (2013.01); *G01N 33/557* (2013.01)

(58) Field of Classification Search
CPC .. G01N 33/557; G01N 21/552; G01N 21/553; G01N 33/543; B01L 2200/148
(Continued)

(56) References Cited

U.S. PATENT DOCUMENTS

| 5,242,828 A | 9/1993 | Bergstroem et al. |
| 5,313,264 A | 5/1994 | Ivarsson et al. |

(Continued)

FOREIGN PATENT DOCUMENTS

| CN | 101297197 A | 10/2008 |
| JP | 2005513496 A | 5/2005 |

(Continued)

OTHER PUBLICATIONS

Nordin, H. et al. "Kinetic studies of small molecule interactions with protein kinases using biosensor technology", Analytical Biochemistry, (2005) 340(2):359-364.*
(Continued)

*Primary Examiner* — Christopher L Chin
(74) *Attorney, Agent, or Firm* — Hanley, Flight and Zimmerman, LLC (57) ABSTRACT

A method of determining one or more interaction parameters for the interaction between an analyte and a ligand using a biosensor, which comprises the steps of: A: providing a sensor surface having the ligand immobilized thereto, B: contacting the sensor surface with a control analyte, C: registering the sensor response from binding of the control analyte to binding sites of the ligand, D: determining the control saturation response ($R_{maxC}$) for the interaction between the control analyte and the ligand, E: transforming the control saturation response ($R_{maxC}$) to an analyte saturation response ($R_{maxA}$) using the relative molar response contribution of the analyte and the control analyte. F: contacting the sensor surface with one or more samples containing different concentrations of the analyte, G: registering the sensor response from binding of the analyte to the binding sites, and H: fitting the registered sensor response to a predetermined interaction model using the analyte saturation response ($R_{maxA}$) to determine the interaction parameters.

8 Claims, 9 Drawing Sheets

(58) Field of Classification Search
USPC .................................................. 436/517, 501
See application file for complete search history.

(56) References Cited

U.S. PATENT DOCUMENTS

| | | | |
|---|---|---|---|
| 5,436,161 | A | 7/1995 | Bergstroem et al. |
| 5,492,840 | A | 2/1996 | Malmqvist et al. |
| 6,093,536 | A | 7/2000 | Drake et al. |
| 6,586,193 | B2* | 7/2003 | Yguerabide et al. ............. 506/3 |
| 7,060,448 | B2* | 6/2006 | Henderson et al. ........... 435/7.1 |
| 8,778,697 | B2* | 7/2014 | Dale et al. .................... 436/501 |
| 2002/0019019 | A1 | 2/2002 | Hamalainen et al. |
| 2002/0142289 | A1 | 10/2002 | Siiman |
| 2002/0182717 | A1* | 12/2002 | Karlsson .................... 435/287.2 |
| 2005/0175999 | A1 | 8/2005 | Klakamp et al. |
| 2005/0255527 | A1* | 11/2005 | Yang et al. ..................... 435/7.1 |
| 2006/0019244 | A1 | 1/2006 | Martinez et al. |
| 2007/0048807 | A1 | 3/2007 | Song |
| 2007/0092973 | A1 | 4/2007 | Potyrailo et al. |
| 2007/0122861 | A1 | 5/2007 | Walt et al. |
| 2008/0299673 | A1 | 12/2008 | Wagner et al. |
| 2011/0262964 | A1* | 10/2011 | Bedouelle ............ G01N 33/533 435/69.1 |
| 2013/0065251 | A1* | 3/2013 | Karlsson et al. ............. 435/7.8 |
| 2016/0165162 | A1* | 6/2016 | Mabuchi ............. H04N 5/3559 348/322 |
| 2016/0243297 | A9* | 8/2016 | Chamney ............... A61B 5/026 |
| 2017/0370927 | A1* | 12/2017 | Dale .................... G01N 33/557 |

FOREIGN PATENT DOCUMENTS

| | | |
|---|---|---|
| JP | 2008-292211 | 12/2008 |
| JP | 2008544248 A | 12/2008 |
| WO | WO 2000/079268 | 12/2000 |
| WO | 2005/029077 | 3/2005 |
| WO | WO 2005/114218 | 12/2005 |
| WO | 2006135309 A2 | 12/2006 |

OTHER PUBLICATIONS

Stenlund, P. et al. "Studies of small molecule interactions with protein phosphatases using biosensor technology", Analytical Biochemistry, (2006) 353:217-225.*
Buhl, A., et al., Biosensors and Bioelectronics, 25 (2009) 198-203.
Katsamba, P., et al., Methods, 26 (2002) 95-104.
EP10833674.4 Search Report dated Aug. 1, 2013.
Notice of Preliminary Rejection dated Mar. 4, 2014 Issued on Corresponding JP Patent Application No. 2012-545420.
Chinese Office Action issued in connection with corresponding CN Application No. 201080053950.0 dated Dec. 16, 2013.
Unofficial English Translation of Japanese Notice of Allowance issued in connection with corresponding JP Application No. 2012545420 dated Dec. 16, 2014.

* cited by examiner

PRIOR ART

Fig. 1

PRIOR ART

METHOD AND SYSTEM FOR MORE RELIABLE DETERMINATION OF INTERACTION PARAMETERS FOR LOW AFFINITY ANALYTES

CROSS-REFERENCE TO RELATED APPLICATIONS

This application is a filing under 35 U.S.C. 371 of international application number PCT/SE2010/051310, filed Nov. 29, 2010, published on Jun. 3, 2011 as WO 2011/065912, which claims priority to application numbers 0950913-4 filed in Sweden on Nov. 30, 2009 and 0951035-5 filed in Sweden on Dec. 30, 2009.

FIELD OF THE INVENTION

The present invention relates to a method of analysing molecular binding interactions at a sensing surface, and more particularly to a method of determining one or more interaction parameters for the interaction between an analyte and a ligand using a biosensor

BACKGROUND OF THE INVENTION

Analytical sensor systems that can monitor interactions between molecules, such as biomolecules, in real time are gaining increasing interest. These systems are often based on optical biosensors and usually referred to as interaction analysis sensors or biospecific interaction analysis sensors. A representative such biosensor system is the BIACORE® instrumentation sold by Biacore AB (Uppsala, Sweden), which uses surface plasmon resonance (SPR) for detecting interactions between molecules in a sample and molecular structures immobilized on a sensing surface. As sample is passed over the sensor surface, the progress of binding directly reflects the rate at which the interaction occurs. Injection of sample is followed by a buffer flow during which the detector response reflects the rate of dissociation of the complex on the surface. A typical output from the BIACORE® system is a graph or curve describing the progress of the molecular interaction with time, including an association phase part and a dissociation phase part. This binding curve, which is usually displayed on a computer screen, is often referred to as a "sensorgram".

With the BIACORE® system (and analogous sensor systems) it is thus possible to determine in real time without the use of labeling, and often without purification of the substances involved, not only the presence and concentration of a particular molecule (analyte) in a sample, but also additional interaction parameters, including kinetic rate constants for binding (association) and dissociation in the molecular interaction as well as the affinity for the surface interaction. The association rate constant ($k_a$) and the dissociation rate constant ($k_d$) can be obtained by fitting the resulting kinetic data for a number of different sample analyte concentrations to mathematical descriptions of interaction models in the form of differential equations. The affinity (expressed as the affinity constant $K_A$ or the dissociation constant $K_D$) can be calculated from the association and dissociation rate constants. Many times, however, it may be difficult to obtain definitive kinetic data, and it is therefore usually more reliable to measure the affinity by equilibrium binding analysis, which involves determining, for a series of analyte concentrations, the level of binding at equilibrium, or steady state, which is presumed to have been reached at or near the end of the association phase of the binding interaction. To ensure that the association phase of the binding curve is indeed likely to have reached steady state, one usually determines in advance the necessary time length of sample injection (i.e. sample contact time with the sensor chip surface) for the bound analyte to reach equilibrium under the conditions intended to be used for the affinity measurements. Since both the time taken to reach equilibrium and the time it takes for the analyte to dissociate are governed primarily by the dissociation rate constant, approximate injection times may also be estimated from the dissociation constant.

SUMMARY OF THE INVENTION

The object of the invention is to provide a new method and biosensor system for determining one or more interaction parameters for the interaction between an analyte and a ligand using a biosensor, which method and biosensor system overcomes one or more drawbacks of the prior art. This is achieved by the method and biosensor system as defined in the independent claims.

One advantage with the method of the present invention is that it allows improved and more reliable determination of interaction parameters for low affinity analytes.

A more complete understanding of the present invention, as well as further features and advantages thereof, will be obtained by reference to the following detailed description and drawings.

DETAILED DESCRIPTION OF THE INVENTION

As mentioned above, the present invention relates to the evaluation of steady state binding data for a molecular binding interaction between a first and a second species to determine the affinity for the interaction, wherein steady state binding data for a binding interaction between the first and a third control species is used to estimate the maximum response $R_{max}$ for the interaction between the first and the second species. Typically, the experimental binding data is obtained by sensor-based technology, which studies the molecular interactions and presents the results in real time as the interactions progress. Before describing the present invention in more detail, however, the general context in which the invention is intended to be used will be described.

Unless defined otherwise, all technical and scientific terms used herein have the same meaning as commonly understood by a person skilled in the art related to this invention. Also, the singular forms "a", "an", and "the" are meant to include plural reference unless it is stated otherwise.

All publications, patent applications, patents, and other references mentioned herein are incorporated by reference in their entirety.

As mentioned above, the present invention relates to the evaluation of steady state binding data for a molecular binding interaction from a plurality of data sets for the interaction to determine one or more interaction parameters for the interaction, wherein other interaction data from a data set than steady state binding data is used to estimate the reliability of the steady state binding data of the data set. Typically, the experimental binding data is obtained by sensor-based technology, which studies the molecular interactions and presents the results in real time as the interactions progress. Before describing the present invention in more detail, however, the general context in which the invention is intended to be used will be described.

Chemical sensors or biosensors are typically based on label-free techniques, detecting a change in a property of a sensor surface, such as e.g. mass, refractive index, or thickness for the immobilised layer, but there are also sensors relying on some kind of labelling. Typical sensor detection techniques include, but are not limited to, mass detection methods, such as optical, thermo-optical and piezoelectric or acoustic wave methods (including e.g. surface acoustic wave (SAW) and quartz crystal microbalance (QCM) methods), and electrochemical methods, such as potentiometric, conductometric, amperometric and capacitance/impedance methods. With regard to optical detection methods, representative methods include those that detect mass surface concentration, such as reflection-optical methods, including both external and internal reflection methods, which are angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors; external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaky mode spectroscopy, reflective interference spectroscopy (RIfS), transmission interferometry, holographic spectroscopy, and atomic force microscopy (AFR).

Commercially available biosensors include the aforementioned BIACORE® system instruments, manufactured and marketed by Biacore AB, Uppsala, Sweden, which are based on surface plasmon resonance (SPR) and permit monitoring of surface binding interactions in real time between a bound ligand and an analyte of interest. In this context, "ligand" is a molecule that has a known or unknown affinity for a given analyte and includes any capturing or catching agent immobilized on the surface, whereas "analyte" includes any specific binding partner thereto.

While in the detailed description and Examples that follow, the present invention is illustrated in the context of SPR spectroscopy, and more particularly the BIACORE® system, it is to be understood that the present invention is not limited to this detection method. Rather, any affinity-based detection method where an analyte binds to a ligand immobilised on a sensing surface may be employed, provided that a change at the sensing surface can be measured which is quantitatively indicative of binding of the analyte to the immobilised ligand thereon.

The phenomenon of SPR is well known, suffice it to say that SPR arises when light is reflected under certain conditions at the interface between two media of different refractive indices, and the interface is coated by a metal film, typically silver or gold. In the BIACORE® instruments, the media are the sample and the glass of a sensor chip, which is contacted with the sample by a microfluidic flow system. The metal film is a thin layer of gold on the chip surface. SPR causes a reduction in the intensity of the reflected light at a specific angle of reflection. This angle of minimum reflected light intensity varies with the refractive index close to the surface on the side opposite from the reflected light, in the BIACORE® system the sample side.

Figure 1:
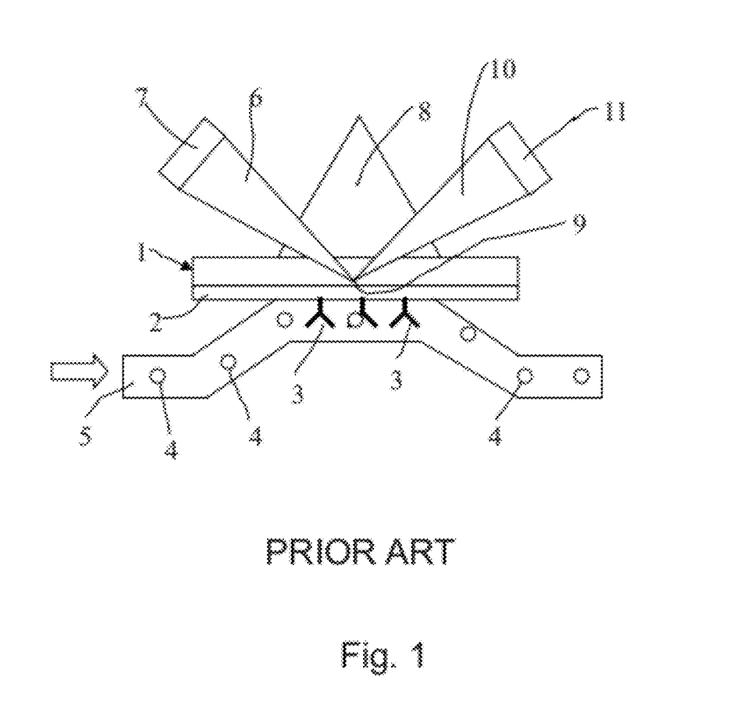
FIG. 1 is a schematic side view of a biosensor system based on SPR.

A schematic illustration of the BIACORE® system is shown in FIG. 1. Sensor chip 1 has a gold film 2 supporting capturing molecules (ligands) 3, e.g. antibodies, exposed to a sample flow with analytes 4, e.g. an antigen, through a flow channel 5. Monochromatic p-polarised light 6 from a light source 7 (LED) is coupled by a prism 8 to the glass/metal interface 9 where the light is totally reflected. The intensity of the reflected light beam 10 is detected by an optical detection unit 11 (photodetector array).

A detailed discussion of the technical aspects of the BIACORE® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE® instruments may be found in U.S. Pat. No. 5,492,840. The teachings of each of the patents mentioned above are incorporated by reference in their entirety. Included are any continuation and divisional applications relative to each of the above patents.

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot, or kinetic or binding curve (binding isotherm), is usually called a sensorgram, also sometimes referred to in the art as "affinity trace" or "affinogram". In the BIACORE® system, the SPR response values are expressed in resonance units (RU). One RU represents a change of 0.0001° in the angle of minimum reflected light intensity, which for most proteins and other biomolecules correspond to a change in concentration of about 1 $pg/mm^2$ on the sensor surface. As sample containing an analyte contacts the sensor surface, the capturing molecule (ligand) bound to the sensor surface interacts with the analyte in a step referred to as "association." This step is indicated on the sensorgram by an increase in RU as the sample is initially brought into contact with the sensor surface. Conversely, "dissociation" normally occurs when the sample flow is replaced by, for example, a buffer flow. This step is indicated on the sensorgram by a drop in RU over time as analyte dissociates from the surface-bound ligand.

Figure 2:
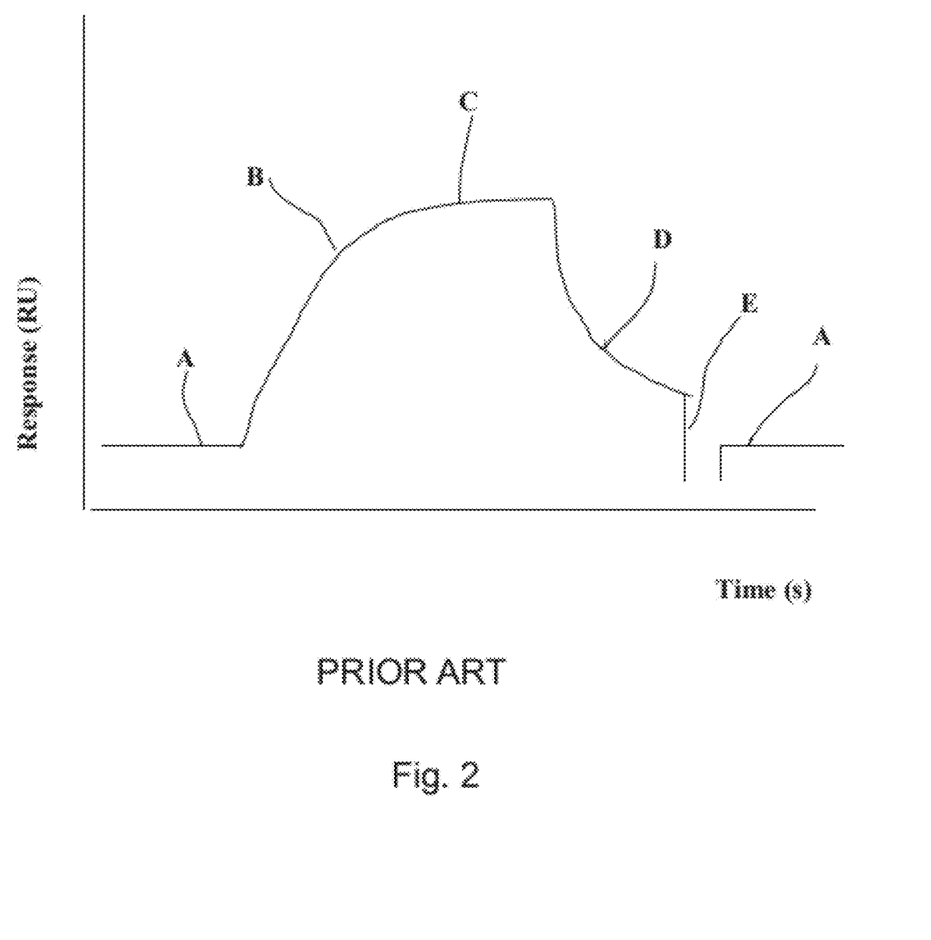
FIG. 2 is a representative sensorgram where the binding curve has visible association and dissociation phases.

A representative sensorgram (binding curve) for a reversible interaction at the sensor chip surface is presented in FIG. 2, the sensing surface having an immobilised capturing molecule, or ligand, for example an antibody, interacting with a binding partner therefore, or analyte, in a sample. The binding curves produced by biosensor systems based on other detection principles mentioned above will have a similar appearance. The vertical axis (y-axis) indicates the response (here in resonance units, RU) and the horizontal axis (x-axis) indicates the time (here in seconds). Initially, buffer is passed over the sensing surface giving the baseline response $\underline{A}$ in the sensorgram. During sample injection, an increase in signal is observed due to binding of the analyte. This part $\underline{B}$ of the binding curve is usually referred to as the "association phase". Eventually, a steady state condition is reached at or near the end of the association phase where the resonance signal plateaus at $\underline{C}$ (this state may, however, not always be achieved). It is to be noted that herein the term "steady state" is used synonymously with the term "equilibrium" (in other contexts the term "equilibrium" may be reserved to describe the ideal interaction model, since in practice binding could be constant over time even if a system is not in equilibrium). At the end of sample injection, the sample is replaced with a continuous flow of buffer and a decrease in signal reflects the dissociation, or release, of analyte from the surface. This part $\underline{D}$ of the binding curve is usually referred to as the "dissociation phase". The analysis is ended by a regeneration step where a solution capable of removing bound analyte from the surface, while (ideally) maintaining the activity of the ligand, is injected over the sensor surface. This is indicated in part $\underline{E}$ of the sensorgram. Injection of buffer restores the baseline $\underline{A}$ and the surface is now ready for a new analysis.

From the profiles of the association and dissociation phases $\underline{B}$ and $\underline{D}$, respectively, information regarding the binding and dissociation kinetics is obtained, and the height of the resonance signal at $\underline{C}$ represents affinity (the response resulting from an interaction being related to the change in mass concentration on the surface). This will now be explained in more detail below.

Surface Binding Rate

Assume a reversible reaction between an analyte A and a surface-bound (immobilised) capturing molecule, or ligand, B which is not diffusion or mass transfer limited and obeys pseudo first order kinetics:

This interaction model (usually referred to as the Langmuir model), which assumes that the analyte (A) is both monovalent and homogenous, that the ligand (B) is homogenous, and that all binding events are independent, is in fact applicable in the vast majority of cases.

The rate of change in surface concentration of analyte A (=rate of change in concentration of formed complex AB) during analyte injection is the sum of the rates of the analyte A going on and off:

$$\frac{d[AB]}{dt} = k_a[A][B] - k_d[AB] \quad (1)$$

where [A] is the concentration of analyte A, [B] is the concentration of the ligand B, [AB] is the concentration of the reaction complex AB, $k_a$ is the association rate constant, and $k_d$ is the dissociation rate constant.

After a time t, the concentration of unbound ligand B at the surface is $[B_T]$-[AB], where $[B_T]$ is the total, or maximum, concentration of ligand B. Insertion into Equation (1) gives:

$$\frac{d[AB]}{dt} = k_a[A]\{[B_T] - [AB]\} - k_d[AB] \quad (2)$$

In terms of detector response units (AB is detected), this can be expressed as $$\frac{dR}{dt} = k_a C(R_{max} - R) - k_d R \quad (3)$$

where R is the response at time t in resonance units (RU), C is the initial, or bulk, concentration of free analyte (A) in solution, and $R_{max}$ is the response (in RU) obtained if analyte (A) had bound to all ligand (B) on the surface, also referred to as the saturation response. Rearrangement of Equation (3) gives:

$$\frac{dR}{dt} = k_a CR_{max} - (k_a C + k_d)R \quad (4)$$

where R is the response in resonance units (RU). In integrated form, the equation is:

$$R = \frac{k_a CR_{max}}{k_a C + k_d}(1 - e^{-(k_a C + k_d)t}) \quad (5)$$

Calculation of $k_a$ and $k_d$

Now, according to equation (4), if dR/dt is plotted against the bound analyte concentration R, the slope is $-(k_a C + k_d)$ and the vertical intercept is $k_a CR_{max}$. If the bulk concentration C is known and the saturation response $R_{max}$ has been determined (e.g. by saturating the surface with a large excess of analyte), the association rate constant $k_a$ and the dissociation rate constant $k_d$ can be calculated. A more convenient method is, however, fitting of the integrated function (5), or numerical calculation and fitting of the differential Equation (4), preferably by means of a computer program.

$k_d$ may also be determined in the following way. The rate of dissociation can be expressed as:

$$\frac{dR}{dt} = -k_d R \quad (6)$$

and in integrated form:

$$R = R_0 \cdot e^{-k_d t} \quad (7)$$

where $R_0$ is the response at the beginning of the dissociation phase (when the buffer wash of the surface starts).

Equation (6) may be linearized:

$$\ln\left[\frac{R}{R_0}\right] = -k_d t \quad (8)$$

and a plot of ln[R/R$_0$] versus t will produce a straight line with the slope=$-k_d$. More conveniently, however, the dissociation rate constant $k_d$ is determined by fitting the exponential rate equation (7).

To obtain reliable kinetic constants, the above described analysis is usually repeated for a number of different analyte concentrations and, suitably, also at least one other ligand density at the sensor surface.

Calculation of Affinity

Affinity is expressed by the association constant $K_A = k_a/k_d$, or the dissociation constant (also referred to as the equilibrium constant) $K_D = k_d/k_a$.

The association constant $K_A$ may alternatively be determined from Equation (3), where dR/dt=0 at equilibrium, giving:

$$k_d R_{eq} = k_a C (R_{max} - R_{eq}) \quad (9)$$

where $R_{eq}$ is the detector response at equilibrium. Since $k_a/k_d = K_A$, insertion in Equation (9) and rearrangement gives:

$$\frac{R_{eq}}{C} = -K_A R_{eq} + K_A R_{max} \quad (10)$$

If binding reactions are performed at multiple concentrations, $K_A$ may be obtained by non-linear curve-fitting of the data. Alternatively, e.g. when the kinetic data is unreliable or association and dissociation are too rapid to measure accurately, $R_{eq}/C$ may be plotted versus $R_{eq}$, which gives the slope=$-K_A$ (Scatchard plot).

Rearrangement of Equation (10) gives:

$$R_{eq} = \frac{K_A C R_{max}}{1 + K_A C} \quad (11)$$

Insertion of $K_A = 1/K_D$ into Equation (11) gives:

$$R_{eq} = \frac{C R_{max}}{K_D + C} \quad (12)$$

Usually, Equation (12) is modified to:

$$R_{eq} = \frac{C R_{max}}{K_D + C} + \text{Offset} \quad (13)$$

where "Offset" is a compensation factor for parallel baseline displacement due to systemic refractive index errors.

Equations (11) and (12) may be modified by introducing a steric interference factor n specifying how many binding sites are on average blocked by one analyte molecule:

$$R_{eq} = \frac{K_A C R_{max}}{1 + K_A C n} \quad (14)$$

$$R_{eq} = \frac{C R_{max}}{K_D + C n} \quad (15)$$

Software-Assisted Analysis

Software for the analysis of kinetic and affinity data is commercially available. Thus, for example, evaluation of kinetic and affinity data produced by the BIACORE® instruments is usually performed with the dedicated BIAevaluation software (supplied by Biacore AB, Uppsala, Sweden) using numerical integration to calculate the differential rate equations and non-linear regression to fit the kinetic and affinity parameters by finding values for the variables that give the closest fit, reducing the sum of squared residuals to a minimum.

Determining affinity constants from measured steady state binding levels with the BIAevaluation software involves the following steps:

(i) obtain steady state binding levels ($R_{eq}$) from report points on the sensorgrams in the steady state region of the curve;

(ii) create a plot of $R_{eq}$ against C; and (iii) fit this plot to a general "Steady state affinity" fitting model (e.g. Equation (13 or 14) to obtain $K_A/K_D$ and $R_{max}$.

The Invention

Figure 3:
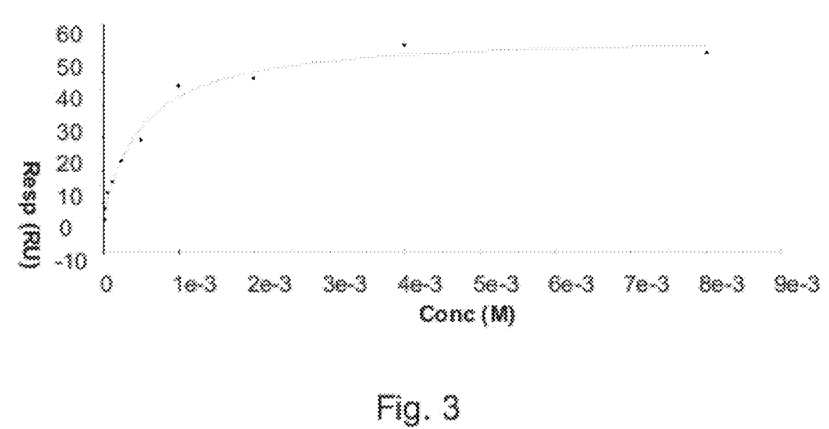
FIG. 3 shows an example of a "normal" affinity analyte curve fit.

As mentioned above, when interaction parameters, such as affinity, and association and dissociation constants, are determined by steady-state analysis with a biosensor, such as a Biacore instrument, a concentration series of the analyte is injected over the immobilized ligand to register the steady state response for the interaction at the different concentrations. Thereafter, the responses are fitted to a predetermined interaction model to determine the interaction parameters. In order to achieve reliable results, the analyte concentrations should extend over a reasonable wide range with respect to the interaction curve. In the prior art, one recommendation is to use analyte concentrations from e.g. 2$K_D$ in a dilution series down to e.g. 0.1$K_D$ to assure coverage of the entire curve, minimizing uncertainties in the fitted parameters. FIG. 3 shows an example of a "normal" affinity analyte curve fit, wherein the data points represents responses with analyte concentrations 0.03$K_D$-16$K_D$, with global fit of the saturation response $R_{max}$:, and wherein the result gives: $K_D$=0.511 mM, and $R_{max}$=57.4 RU.

Figure 4:
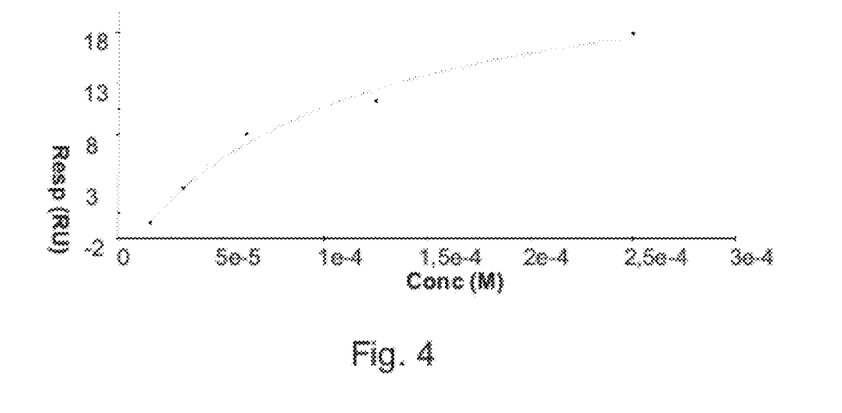
FIG. 4 shows an example of a "low" affinity analyte curve fit based on the lower range of the data points of FIG. 3.

It is however not always feasible to provide analyte concentrations over such a wide range, e.g. due to limitations in the solubility of the analyte or the like. The problem is accentuated when determining low affinities which are common when working with fragment based drug design. Using high analyte concentrations also increase the probability of secondary (non-specific) interactions with the surface that will further complicate the evaluation. Under these circumstances only low concentrations (<$K_D$) are possible to use, making the highest response that may be achieved much lower than the $R_{max}$ and the resulting registered response curve will display only little curvature in the plot, both of which introduce uncertainties in the fitted parameters i.e. $K_D$ and $R_{max}$. FIG. 4 shows an example of a "low" affinity analyte curve fit based on the lower range of the data points of FIG. 3, using only the five lowest data points in the data set. In this example, the fit gives $K_D$=0.109 mM, $R_{max}$=30.9 RU, whereby both the affinity $K_D$ and the saturation response $R_{max}$ values deviates significantly from the above values when all points are used (compare with FIG. 3).

Since the saturation response $R_{max}$ is a parameter related to the surface i.e. the immobilized interactant and not to the analyte, it has been found that the saturation response for such an analyte, $R_{maxA}$ may be determined using a suitable second analyte (control analyte) in a separate experiment. The control analyte saturation response value referred to as $R_{maxC}$ may subsequently, after adjustment for differences in relative response (or molecular weight) between control and sample analytes, be used as a constant when evaluating experiments with low concentrations (relative to the affinity $K_D$) of analytes.

Figure 5:
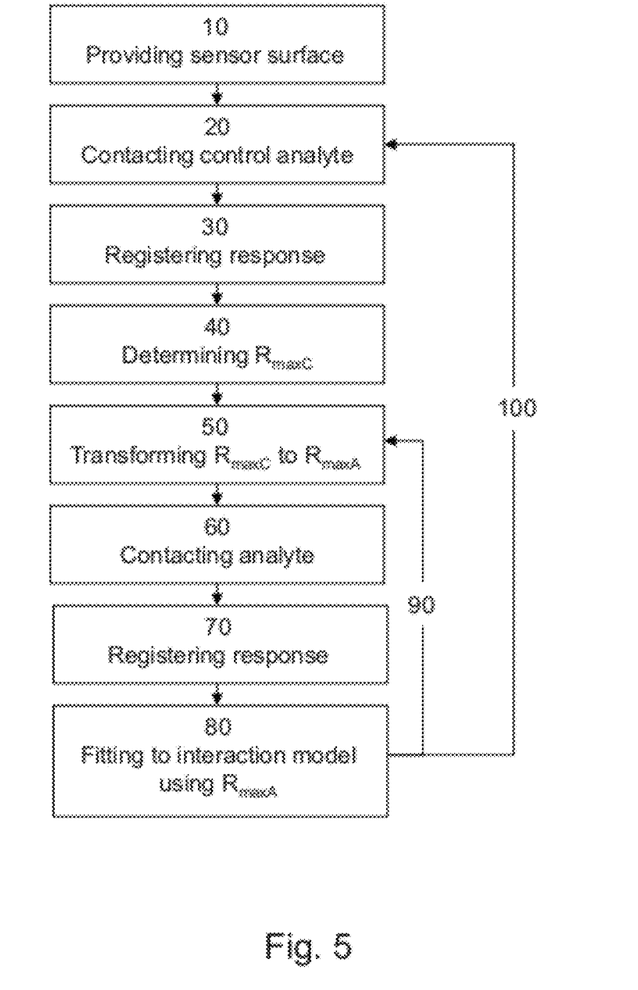
FIG. 5 shows a schematic block diagram of a method according to one embodiment of the present invention.

According to one embodiment of the present invention, schematically shown in FIG. 5, there is provided a method of determining one or more interaction parameters for the interaction between an analyte and a ligand using a biosensor, which comprises the steps of:

A: providing a sensor surface having the ligand immobilized thereto, FIG. 5 ref. 10,
B: contacting the sensor surface with a control analyte, FIG. 5 ref. 20,
C: registering the sensor response from binding of the control analyte to binding sites of the ligand, FIG. 5 ref. 30,
D: determining the control saturation response ($R_{maxC}$) for the interaction between the control analyte and the ligand, FIG. 5 ref. 40
E: transforming the control saturation response ($R_{maxC}$) to an analyte saturation response ($R_{maxA}$) using the relative molar response contribution of the analyte and the control analyte, FIG. 5 ref. 50,
F: contacting the sensor surface with one or more samples containing different concentrations of the analyte, FIG. 5 ref. 60,
G: registering the sensor response from binding of the analyte to the binding sites, FIG. 5 ref. 70, and
H: fitting the registered sensor response to a predetermined interaction model using the analyte saturation response ($R_{maxA}$) to determine the interaction parameters, FIG. 5 ref. 80.

As is discussed above, the interaction parameters may be any parameters characterizing the interaction between the ligand and the analyte, such as the affinity (e.g. $K_A$ or $K_D$), a kinetic constant (e.g. $k_a$ or $k_d$). The method may be performed using any suitable biosensor as exemplified above, and the interaction parameter indicators, e.g. $K_A$, $K_D$, $k_a$ or $k_d$ may be different depending on the field of the biosensor.

Step A of providing a sensor surface having the ligand immobilized thereto involves any suitable ways of immobilizing the ligand to a sensor surface in the particular biosensor used. The immobilized ligand providing binding sites for the control analyte and the analytes to be investigated. In step B, a suitable control analyte is put in contact with the sensor surface. According to above, the control analyte should be selected so that the control saturation response ($R_{maxC}$) for the interaction between the control analyte and the ligand can be readily determined. For example, the control analyte should have a higher soulubility, with respect to the affinity $K_D$, compared to the analytes to be investigated. According to one embodiment, the control analyte is provided at a concentration such that it is capable of occupying all binding sites of the ligand on the sensor surface to provide a direct determination of the control saturation response ($R_{maxC}$) from one interaction event. Alternatively, the control analyte is provided at a concentration range such that it is possible to determine the control saturation response ($R_{maxC}$) from a non steady state interaction between the control analyte and the ligand.

In step E of transforming the control saturation response ($R_{maxC}$) to an analyte saturation response ($R_{maxA}$), the fact that the saturation response ($R_{max}$) for each analyte represents the response when all binding sites are occupied, is used for the transformation. By using the same sensor surface for determining the saturation response ($R_{max}$) for two different analytes, e.g. analytes S and T respectively, ideally the saturation responses ($R_{maxS}$) and ($R_{maxT}$) respectively represents the response resulting from the same number of molecules bound to the sensor surface. Hence, the saturation responses ($R_{maxS}$) and ($R_{maxT}$) registered using the same sensor surface gives the relative molar response contribution for the two analytes. Therefore, taken that the relative molar response contribution for two analytes is known or can be estimated, then the saturation response ($R_{max}$) for one analyte may be calculated (estimated) from the saturation response ($R_{max}$) of the other analyte. According to the present invention this relationship is used to transform the control saturation response ($R_{maxC}$) to an analyte saturation response ($R_{maxA}$).

As mentioned above, there are a number of biosensors available based on a number of different detection techniques, therefore the relative molar response of two different analytes depends on the biosensor used, but the principle is still valid. According to one embodiment, the relative molar response contribution of the analyte and the control analyte in step E is approximated by the molar weight ratio between the analyte and the control analyte. This approach is valid, or at least a good approximation, for any biosensor technique that directly or indirectly registers the mass of the molecules bond to the sensor surface.

According to one embodiment, the dissociation rate of the control analyte is sufficiently high to reach complete dissociation within a reasonable timeframe after replacing the control analyte with a sample free from analyte capable of binding to the sensor surface, e.g. buffer. Alternatively a step of regeneration may be necessary to free all binding sites in between the analytes. According to one embodiment, steps E to H are repeated for a plurality of analytes in order to determine one or more interaction parameters for each of the plurality of analytes based on a saturation response ($R_{maxA}$) calculated for each analyte, indicated by ref 90 in FIG. 5. In order to detect and/or correct for possible degeneration of the sensor surface over time, steps B to D may be repeated after steps E to H have been performed for a predetermined number of analytes, indicated by ref 100 in FIG. 5.

According to one embodiment there is provided an analytical system for detecting molecular binding interactions, comprising:
(i) a biosensor comprising at least one sensing surface, detection means for detecting molecular binding interactions at the at least one sensing surface, and means for producing detection data representing binding curves, wherein each curve represents the progress of a binding interaction with time, and
(ii) data processing means for performing steps A to H of the above method.

The invention also extends to computer programs, particularly computer programs on or in a carrier, adapted for putting the method of the invention into practice. The carrier may be any entity or device capable of carrying the program. For example, the carrier may comprise a storage medium, such as a ROM, a CD ROM, a DVD or a semiconductor ROM, or a magnetic recording medium, for example a floppy disc or a hard disk. The carrier may also be a transmissible carrier, such as an electrical or optical signal which may be conveyed via electrical or optical cable or by radio or other means. Alternatively, the carrier may be an integrated circuit in which the program is embedded. Any medium known or developed that can store information suitable for use with a computer system may be used.

Figure 6:
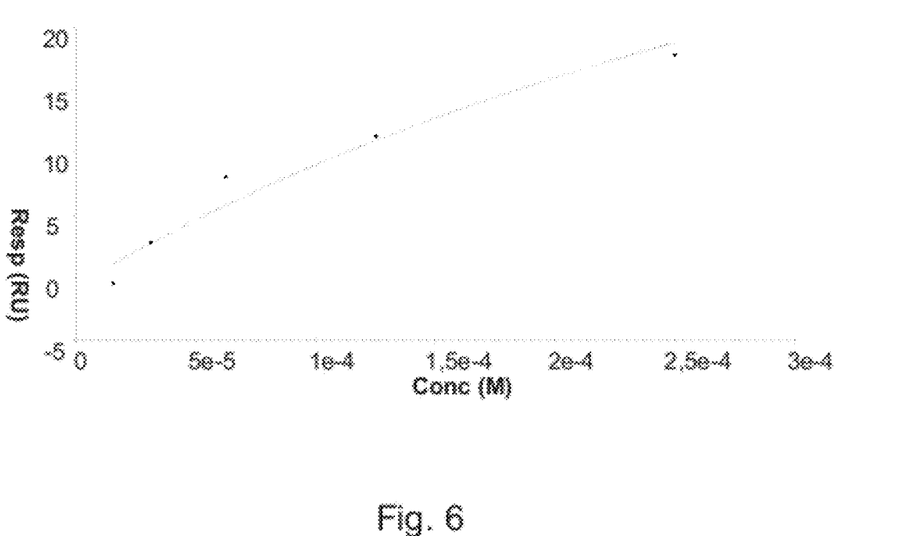
FIG. 6 shows a corresponding fit as in FIG. 4.

FIG. 6 shows a corresponding fit as in FIG. 4. The same data points as in FIG. 4 but fitted with a constant $R_{max}$ of 60 RU determined in a separate experiment using a control analyte, whereby $K_D$=0.52 mM. FIGS. 4 and 6 together exemplifies a case were a fit to a few points in a remote interval can give a misleading good fit (FIG. 4) resulting in erroneously determined parameters. By the use of a pre determined control saturation response $R_{maxC}$ according to the present invention this can be avoided and the right affinity is determined (FIG. 6).

It has been shown that this is a powerful approach for accurate determination of low affinities e.g. down to $K_D$=0.5 mM or lower. It has also been show that the relative advantage of the method increases when fewer data points are used for the evaluation.

Figure 7A:
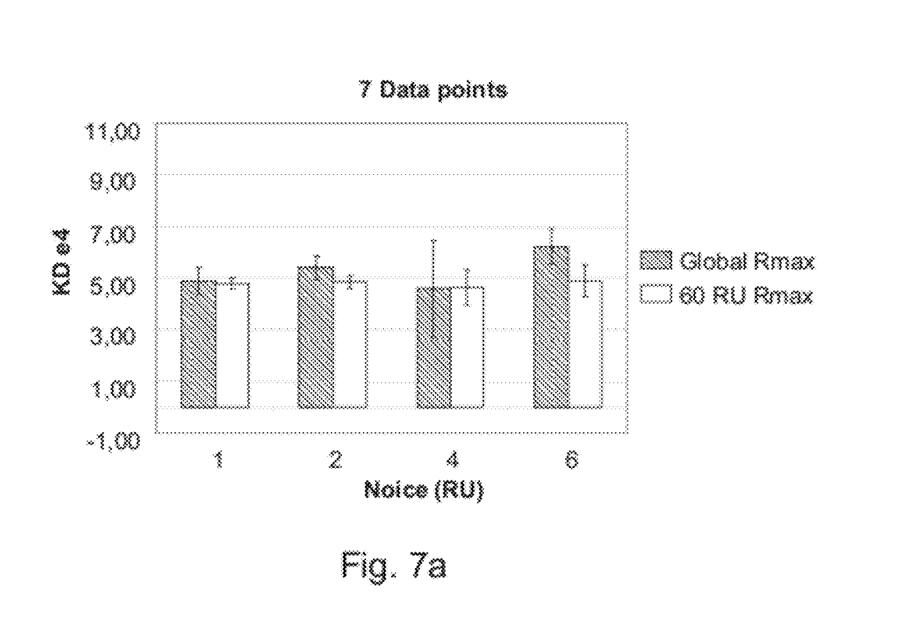
FIGS. 7a-7c show fittings of simulated data sets with various levels of method noise.
Figure 7B:
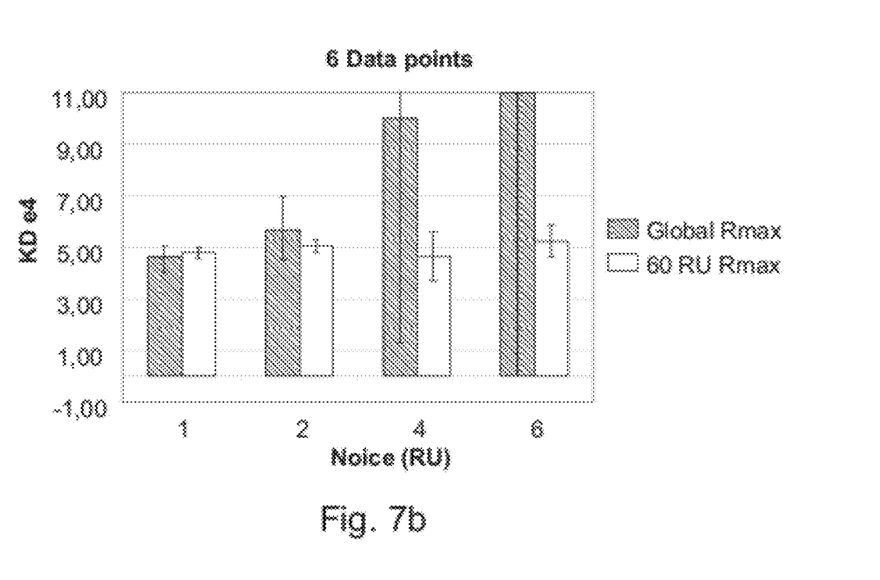
Figure 7C:
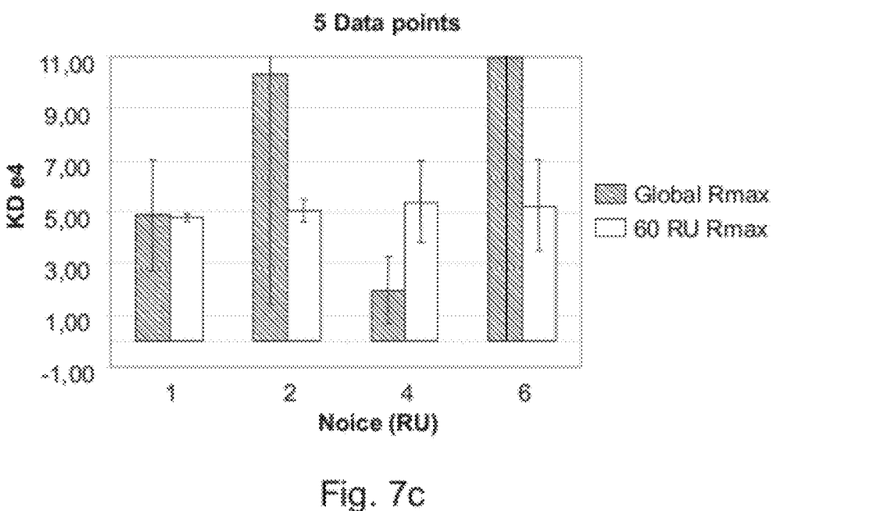

FIGS. 7a-7c show fittings of simulated data sets with various levels of method noise, 1-6 RU using 7, 6 or 5 data points. Dashed bars represents $K_D$ from fits with varying $R_{max}$ and white bars $K_D$ from fits with $R_{max}$ set to 60 RU, which is the simulation value. The simulated affinity is: $K_D$=5×10$^{-4}$M. Error bars represents +/−1 standard deviation within triplicates.

It has further been found that this approach may be used for fitting data sets with secondary interactions with the equation:

$$R_{eq} = \frac{CR_{max1}}{K_{D1} + C} + \frac{CR_{max2}}{K_{D2} + C} + \text{offset} \quad (17)$$

Figure 8A:
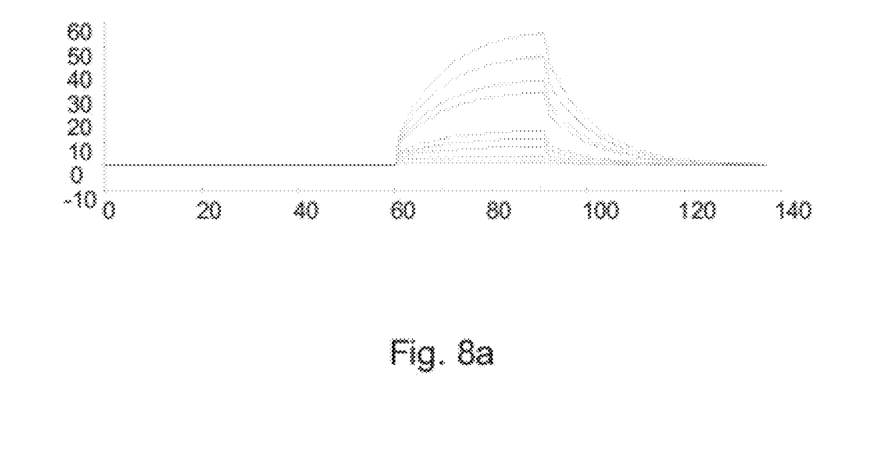
FIGS. 8a and 8b show fitting to simulated data set with secondary very low affinity (non-specific) binding.
Figure 8B:
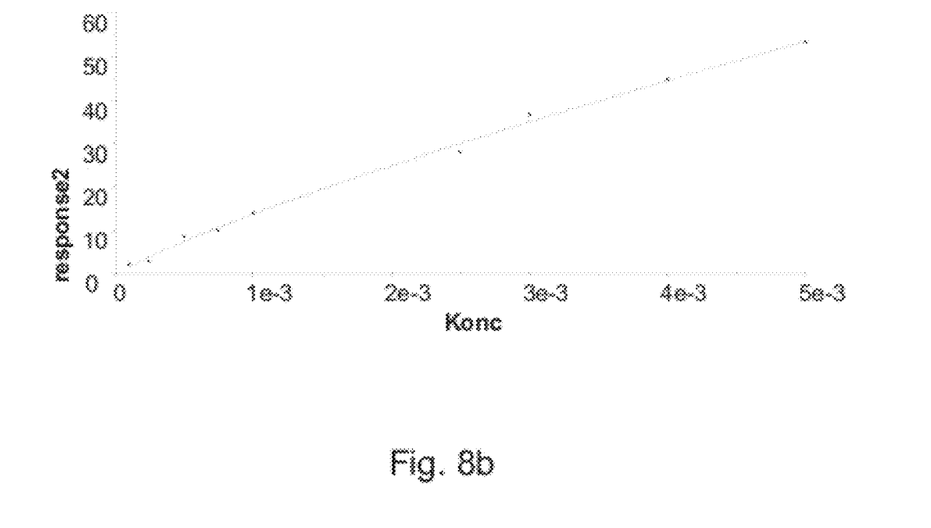

If setting a predetermined $R_{max1}$ as constant, the affinity ($K_{D1}$) for the appropriate interaction can be readily determined. FIGS. 8a and 8b show fitting to simulated data set with secondary very low affinity (non-specific) binding. The simulated specific $K_D$=1 mM could be calculated ($K_D$=1.7 mM+/−0.45, n=7) when the simulated corresponding $R_{max}$ were set as constant. The simulated method noise was 2 RU or 20% of $R_{max}$ which is relatively high.

Binding Behaviour Evaluation

According to one embodiment of the invention there is provided a method of evaluating the quality of the fit of the registered sensor response to a predetermined 1:1 binding interaction model to determine the interaction parameters, comprising the steps:

I. Selecting method of determining $R_{max}$ for each analyte. The available choices, may e.g. be global determination of $R_{max}$ from registered sensor response at different concentrations of the analyte, and determination of $R_{maxA}$ according to the above method using a control analyte and the associated $R_{maxC}$.

J. Evaluating the binding behavior of the analyte-ligand interaction by one or more binding behavior criteria selected from the group of:
  a). High registered R
  b) Elevated baseline after injection
  c) Increasing response during injection
  d) Ratio between $R_{maxGlobal}$ and $R_{maxA}$ K. Based on the evaluation in step ii) suggesting binding model to be used for calculation of the interaction parameter(s) of each analyte.

According to one embodiment, the binding behavior criteria a) is a control whether the registered maximum response exceeds a predetermined value for the analyte interaction: "high R". This criteria is related to if the response exceeds the calculated or measured saturation response value for the analyte interaction. $R_{max}$ (or $R_{maxA}$) (at stochiometry 1:1) is compared with registered maximum response for the analyte. If the response registered R for one or more analyte concentrations exceed $R_{max}$+xRU, where x is a value that is selected on basis of the specific interaction that is studied, the analyte concentrations, the ligand density on the sensor surface etc. Depending on the interaction, the value may e.g. be any suitable value between 1 and 500 such as 10, 50, 100, 200 or 400, then the analyte is classified as "High registered R", which is used as an indication of an alternative stoichiometry or additional aggregative interactions whereby a multi-site model should may provide a better fit.

Figure 9:
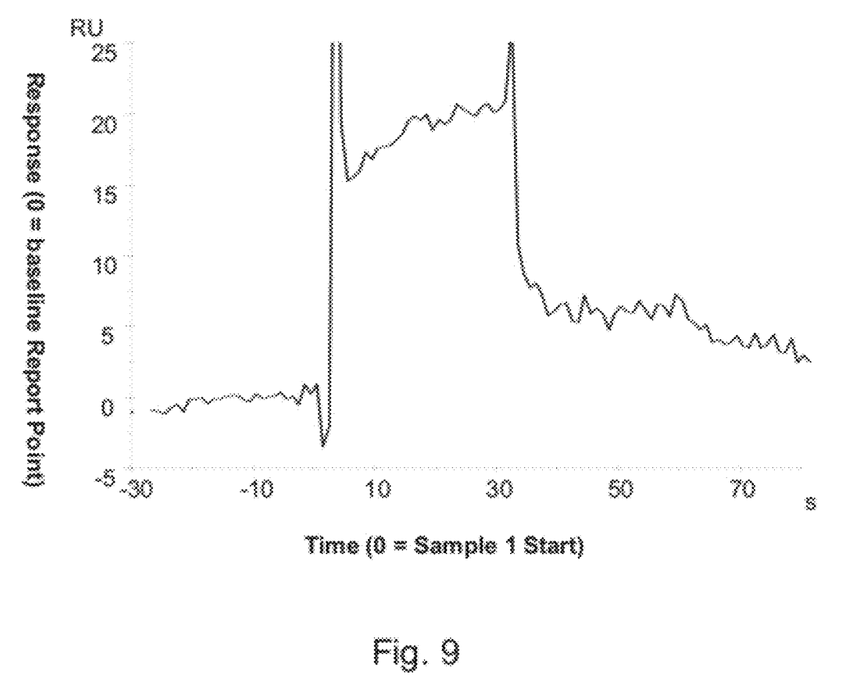
FIG. 9 shows an example of a response curve, which has an elevated baseline after the injection.

According to one embodiment, the binding behavior criteria b) is a control whether the registered response exceeds a predetermined value after the analyte has been in contact with the sensor surface. FIG. 9 shows an example of a response curve that meet this type of criteria which has an elevated baseline after the injection. The predetermined value, may be a globally fixed value in RU units, such as 1 to 500 RU or any value there between, depending on the interactions that are studied. Alternatively, the predetermined value may be a value that is determined based on the registered response of the specific analyte or an average from a range of analytes. According to one embodiment, the predetermined value may be 3 RU. The presence of an elevated baseline after the injection may indicate a tight non-typical binding (for specific fragment) or aggregation, whereby a multi-site model should provide a better fit.

Figure 10:
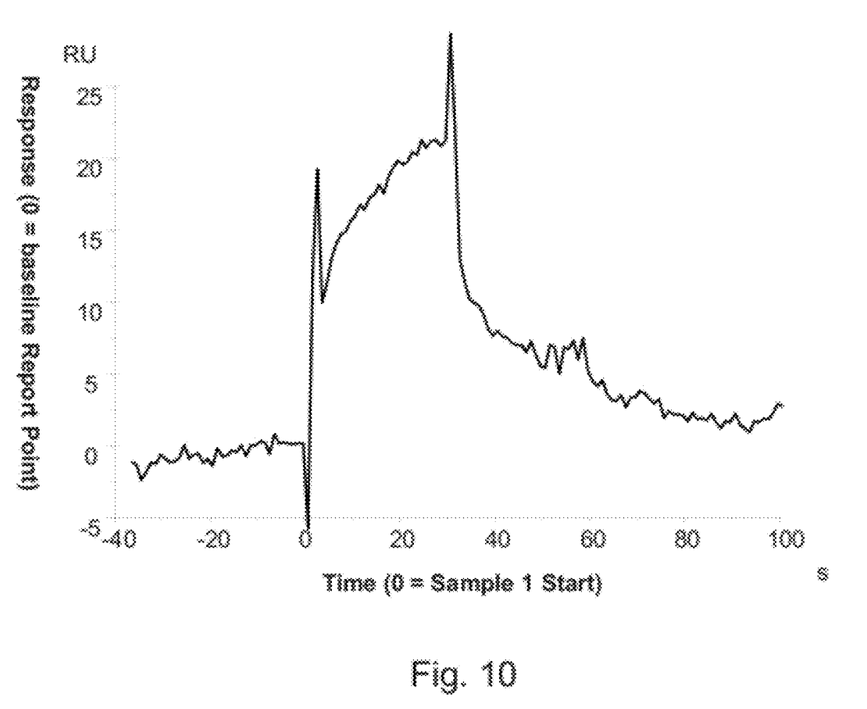
FIG. 10 shows an example of a response curve that displays an increasing response during the injection.

According to one embodiment, the binding behavior criteria c) is that the registered response increases at a rate exceeding a predetermined rate during analyte contact time, such as 0.1 to 150 RU/s or any value there between. FIG. 10 shows an example of a response curve that display an increasing response during the injection, and one example of a criterion for the predetermined rate that may be used is for example >0.2 RU/s. Such a behavior might indicate secondary interactions that take place in addition to the interaction of study, whereby a multi-site model may provide a better fit.

According to one embodiment, the saturation response value $R_{max}$ is calculated both by global determination from registered sensor response at different concentrations of the analyte ($R_{maxGlobal}$) and determination of $R_{maxA}$ according to the above method using a control analyte and the associated $R_{maxC}$, irrespective which method was selected in step I. Thereafter the two results are compared as binding behavior criteria d), e.g. by calculating the relation: n=$R_{maxGlobal}$/$R_{maxA}$ and where n is evaluated as an indicator of binding behavior with respect to one or more predetermined limits. According one embodiment the limit is selected as:

| n < 1.5 | indicates 1:1 binding |
| n > 1.5 | indicates multi site binding |

As is shown above, in some situations the calculation of $R_{maxGlobal}$ may produce a very high value even though the highest registered response R is moderately high, e.g. due to few data points of registered sensor response at different concentrations of the analyte indicating a steep slope. In such situations the resulting value of $R_{maxGlobal}$ may become very high compared to $R_{maxA}$ even though the interaction as such may be a 1:1 binding. Therefore a second criteria limit for the ratio n may e.g. selected as:

n>10 and R<$R_{maxA}$-indicates high R and that 1:1 binding cannot be out ruled

The limit values referred to in above criteria may obviously be varied to achieve the desired effect and without departing from the present invention.

According to one embodiment of the present invention, step K may involve a summary criteria for suggesting an alternative binding model, such as a multi-site model, wherein the number of binding behavior criteria that are met are counted, and if the sum exceeds a predetermined value, an alternative binding model is suggested. According to one embodiment of the present invention, the summary criteria of step K may involve a weighted sum of the binding behavior criteria, wherein the criteria a to d are given an associated weighting factor. According to one embodiment, binding behavior criteria a and d are given weight 2, criteria b to c weight 1, and the summary criteria is set to 2.

Hence, by the practice of determining the $R_{maxC}$ for a prepared surface with an analyte that allows adequate concentrations to be used confidence in analysis of analytes with very low affinity can be achieved.

It is to be understood that the invention is not limited to the particular embodiments of the invention described above, but the scope of the invention will be established by the appended claims.

The invention claimed is:

1. A method of determining one or more interaction parameters for an interaction between a ligand and a sample analyte having a low affinity with respect to the ligand using a biosensor such that the sample analyte is not able to provide a measurable sample analyte saturation response, the method comprising:
   A: (i) registering a first sensor response from binding of a control analyte to binding sites of the ligand to obtain a control analyte saturation response,
      (ii) wherein the ligand is immobilized on a sensor surface,
      (iii) wherein the control analyte is different from the sample analyte,
      (iv) wherein the control analyte has a higher affinity with respect to the ligand than the sample analyte such that the control analyte is to bind to the ligand to provide the control analyte saturation response, and
      (v) wherein the control analyte contacting the sensor surface is to be provided in a concentration selected for measurable determination of the control analyte saturation response from the group consisting of:
      1) a concentration to occupy binding sites of the ligand on the sensor surface to provide a direct determination of the control analyte saturation response ($R_{maxC}$) from one interaction event,
      2) a concentration range to provide a steady state binding interaction between the ligand and the control analyte to determine the control analyte saturation response ($R_{maxC}$), and
      3) a concentration range to provide a determination of the control analyte saturation response ($R_{maxC}$) from a non-steady state interaction between the control analyte and the ligand;
   B: determining the control analyte saturation response ($R_{maxC}$) for the interaction between the control analyte and the ligand;
   C: transforming the control analyte saturation response ($R_{maxC}$) to a sample analyte saturation response ($R_{maxA}$) using a relative molar response contribution of the analyte and the control analyte;
   D: registering a second sensor response from binding of the sample analyte to the binding sites of the ligand immobilized on the same sensor surface, the sample analyte contacting the sensor surface via one or more samples containing different concentrations of the sample analyte; and
   E: fitting the registered second sensor response to a predetermined interaction model using the sample analyte saturation response ($R_{maxA}$) to determine the one or more interaction parameters including at least one of affinity or kinetic rate constants for association and dissociation.

2. The method of claim 1, wherein the relative molar response contribution of the sample analyte and the control analyte in C is approximated by a molar weight ratio between the sample analyte and the control analyte.

3. The method of claim 1, wherein C through E are repeated for a plurality of sample analytes.

4. The method of claim 3, wherein A through B are repeated after C through E have been performed for a predetermined number of sample analytes.

5. The method of claim 1, further comprising:
   I: selecting a method of determining $R_{max}$ for each sample analyte, from global determination of $R_{maxGlobal}$ from the registered second sensor response at different concentrations of the sample analyte, and determination of $R_{maxA}$ using the control analyte and the associated $R_{maxC}$;
   J: evaluating a binding behavior of the analyte-ligand interaction by one or more binding behavior criteria selected from the group of:
      a) High registered R in which a response R for one or more analyte concentrations exceeds a saturation response value for the respective analyte;
      b) Elevated baseline above a predetermined value after injection;
      c) Increasing response exceeding a predetermined rate during injection; and
      d) Ratio between $R_{maxGlobal}$ and $R_{maxA}$; and
   K: suggesting a binding model to be used for calculation of the one or more interaction parameters of each analyte based on the evaluation in J.

6. The method of claim 5, wherein, when a number of satisfied binding behavior criteria exceed a predetermined value, an alternative binding model is provided.

7. The method of claim 1, wherein the biosensor includes a gold film to capture the ligand exposed to the sample analyte and a glass/metal interface to reflect incident polarized light from a light source for detection by a photodetector array.

8. The method of claim 1, wherein the concentration of the sample analyte is less than a dissociation constant $K_D$ between the sample analyte and the ligand.

* * * * *